United States Patent
Falck et al.

(10) Patent No.: US 11,951,083 B2
(45) Date of Patent: Apr. 9, 2024

(54) METHODS OF MANUFACTURING 14,15-EPOXYEICOSATRIENOIC ACID ANALOGS AND IMPROVED THERAPEUTIC DELIVERY OF SAME

(71) Applicant: Cytometix, Inc., Wauwatosa, WI (US)

(72) Inventors: John R. Falck, University Park, CA (US); Lane Brostrom, Eden, UT (US)

(73) Assignee: Cytometix, Inc., Wauwatosa, WI (US)

( * ) Notice: Subject to any disclaimer, the term of this patent is extended or adjusted under 35 U.S.C. 154(b) by 0 days.

(21) Appl. No.: 17/867,352

(22) Filed: Jul. 18, 2022

(65) Prior Publication Data

US 2023/0398086 A1 Dec. 14, 2023

Related U.S. Application Data

(60) Provisional application No. 63/350,347, filed on Jun. 8, 2022.

(51) Int. Cl.

| | |
|---|---|
| *A61K 31/16* | (2006.01) |
| *A61K 9/127* | (2006.01) |
| *A61K 47/10* | (2017.01) |
| *A61K 47/24* | (2006.01) |
| *A61K 47/28* | (2006.01) |
| *C07C 231/14* | (2006.01) |

(52) U.S. Cl.
CPC .............. *A61K 31/16* (2013.01); *A61K 9/127* (2013.01); *A61K 47/10* (2013.01); *A61K 47/24* (2013.01); *A61K 47/28* (2013.01); *C07C 231/14* (2013.01); *C07B 2200/13* (2013.01); *C07C 2601/02* (2017.05)

(58) Field of Classification Search
CPC ........ A61K 31/16; A61K 9/127; A61K 47/10; A61K 47/24; A61K 47/28; C07C 231/14; C07C 2601/02; C07B 2200/13
See application file for complete search history.

(56) References Cited

U.S. PATENT DOCUMENTS 8,658,632 B2 * 2/2014 Brostrom .............. C07C 237/22
514/183
10,966,937 B2 4/2021 Brostrom et al.

FOREIGN PATENT DOCUMENTS

| DE | 4446877 A1 * | 7/1996 | ............ C07B 41/04 |
| WO | WO-9309669 A1 * | 5/1993 | ............ A01N 37/02 |
| WO | 2011066414 | 6/2011 | |
| WO | 2016179137 | 11/2016 | |

OTHER PUBLICATIONS

Sinal et al. The Journal of Biological Chemistry, 2000, vol. 275, No. 51, 40504-40510 (Year: 2000).*
Filopoulou et al. Molecules, 2021, 26, 6005 (Year: 2021).*
Palmieri et al. Beilstein J. Org. Chem, 2013, 9: 533-536 (Year: 2013).*
Diggle et al. Chemical Communications, 1969, 819-820 (Year: 1969).*
Binder et al. Tetrahedron Lett. 2008, 49(17): 2764-2767 (Year: 2008).*
Vaidhyanathan. Journal of Molecular Structure, 608, 2002, 123-133 (Year: 2002).*
Moustaskis. J. Am. Chem. Soc. 1985, 107, 5285-5286 (Year: 1985).*
Capdevila. Tetrahedron Letters, 1994, vol. 35, No. 37, p. 6791-6794 (Year: 1994).*
Saito. Org. Biomol. Chem. 2018, 16, 7636-7647 (Year: 2018).*

* cited by examiner

*Primary Examiner* — Mark L Shibuya
*Assistant Examiner* — Luisalberto Gonzalez
(74) *Attorney, Agent, or Firm* — Fish IP Law, LLP

(57) ABSTRACT

Systems, compositions, and methods are disclosed for developing and delivering therapeutically effective 14,15-epoxyeicosatrienoic acid (14,15-EET) analogs, for example for pain management or treatment. Of particular interest are intermediate salts.

24 Claims, 7 Drawing Sheets

METHODS OF MANUFACTURING 14,15-EPOXYEICOSATRIENOIC ACID ANALOGS AND IMPROVED THERAPEUTIC DELIVERY OF SAME

This application claims the benefit of priority to and is a continuation of U.S. provisional patent application No. 63/350,347, filed on Jun. 8, 2022. This and all other extrinsic references referenced herein are incorporated by reference in their entirety.

FIELD OF THE INVENTION

The field of the invention is therapeutic compounds.

BACKGROUND

The background description includes information that may be useful in understanding the present invention. It is not an admission that any of the information provided herein is prior art or relevant to the presently claimed invention, or that any publication specifically or implicitly referenced is prior art.

Finding new, affordable, and effective methods and treatments for pain is highly desirable. To that end, some arachidonic acid (AA) metabolites, e.g., 14,15-epoxyeicosatrienoic acid (14,15-EET) and analogs, and compositions containing such analogs have been pursued for analgesic treatments. For example, U.S. Pat. No. 8,658,632 to Brostrom et al. ('632 patent) teaches various methods of manufacturing 14,15-EET analogs and pharmaceutical formulations. However, the methods of '632 patent are not optimized and include expensive bottleneck processes, for example chromatography. Further improvements to manufacturing methods are needed to improve production time, efficiency, and scalability, and to reduce costs.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Even with improved manufacturing methods to produce 14,15-EET analogs, delivery methods of such analogs are needed and are favorably optimized to improve therapeutic effect. For example, U.S. Pat. No. 10,966,937 to Brostrom et al. ('937 patent) pursues delivery systems incorporating polyunsaturated fatty acids, their metabolites and derivatives, other additives, and one or more 14,15-EET analogs. However, further development is needed to improve the therapeutic effect of 14,15-EET analogs, for example in treating pain. It is contemplated that improved half-life of delivered 14,15-EET analogs in a patient is a key performance metric.

Thus, there remains a need for systems, methods, and compositions to improve efficiency and cost of developing therapeutic 14,15-EET analogs, and improved delivery systems to optimize therapeutic effects of such 14,15-EET analogs.

SUMMARY OF THE INVENTION

The inventive subject matter provides systems, compositions, and methods for developing and delivering therapeutically effective 14,15-epoxyeicosatrienoic acid (14,15-EET) analogs, for example for pain management or treatment. Methods of providing an intermediate salt, for example a salt of compound 2, are contemplated, including at least in part Reaction I.

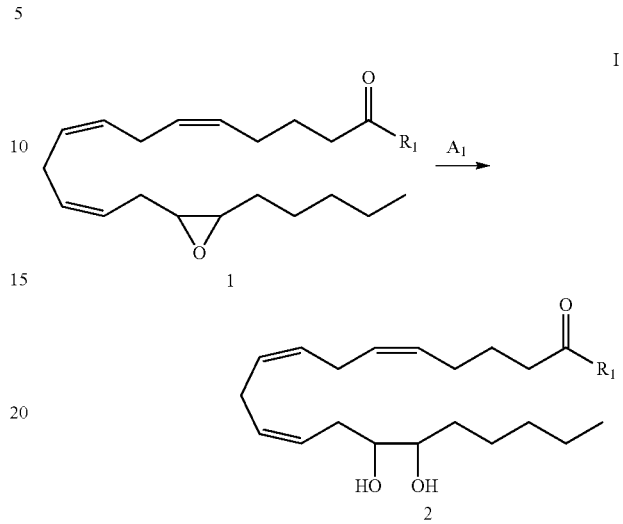

$R_1$ is typically a hydroxyl group, and $A_1$ applies one or more acids to compound 1, producing compound 2. A metal (e.g., alkali metal, alkali earth metal, etc.) base or an amine base is used with compound 2 to form the intermediate salt. Preferably, the intermediate salt is in crystalline form. The acid of $A_1$ is preferably triflic or mesic acid, but other suitable acids are contemplated. Where an amine is combined with compound 2 to form the intermediate salt, it is preferably (1R,2R)-(−)-1-amino-2-indanol, its enantiomer, scalemic or racemic mixture. While this embodiment applies an acid in step $A_1$, in some embodiments an appropriate enzyme is applied (e.g., epoxide hydrolase, etc), for example to form a diol.

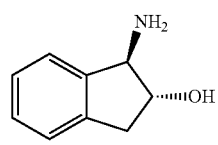 [SMILES: N[C@@H]1c2ccccc2C[C@H]1O]

Where more than one amine is used to complex with more than one compound 2, the amine can be present in racemic or scalemic ratios. Other primary, secondary, or tertiary amines are also contemplated. Where a metal base is combined with compound 2 to form the intermediate salt, it is typically one of a Group I or Group II, excluding francium, radium, and hydrogen. Magnesium, cesium, nickel, or zinc bases could also be used as the metal base.

Further methods of providing an intermediate salt are contemplated, including at least in part Reaction II.

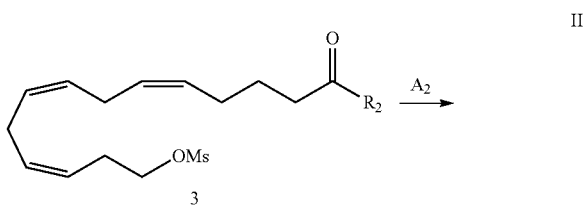

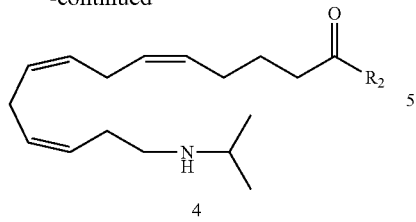

4

$R_2$ is typically a $C_3$-$C_6$ cycloalkyl substituted amine or a $C_5$-$C_6$ cycloalkenyl substituted amine (excluding enamines), and $A_2$ utilizes isopropylamine or an isopropylamine salt with compound 3, in some embodiments in combination with a suitable base, producing compound 4. An acid is used with compound 4 to form the intermediate salt, preferably in crystalline form. The intermediate salt is typically an oxalate salt or a tosylate salt, but can also be an acetate salt, a citrate salt, a nitrate salt, a phosphate salt, a sulfate salt, or a triflate salt. Likewise, the acid used with compound 4 is typically oxalic acid or tosylic acid, but can also be a mineral acid (e.g., HCl, $H_2SO_4$, etc.), another carboxylic acid, acids having a phenyl group (e.g., picric acid, etc.), or other suitable acid. In preferred embodiments, the amine of $A_2$ is isopropylamine or isopropylamine salt plus suitable base. In one preferred embodiment, $R_2$ is In another embodiment, $R_2$ is an ester, e.g., $R_2$=OMe.

DETAILED DESCRIPTION

Figure 1:
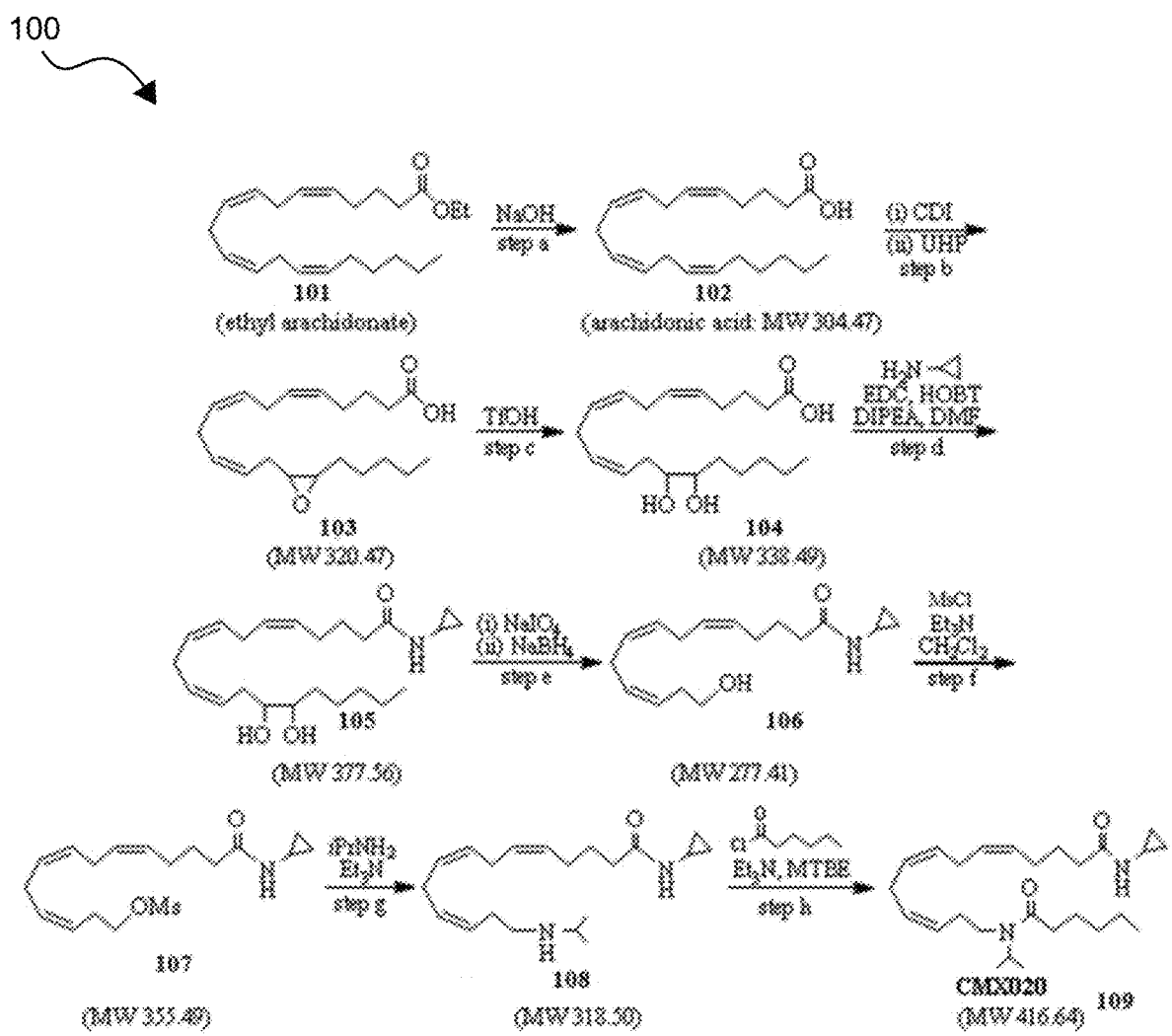
FIG. 1 depicts a scheme for producing a compound of the inventive subject matter.

The inventive subject matter provides systems, compositions, and methods for developing and delivering therapeutically effective 14,15-epoxyeicosatrienoic acid (14,15-EET) analogs, for example for pain management or treatment. For example, methods of providing compound CMX020 are contemplated. CMX020 has the following chemical structure:

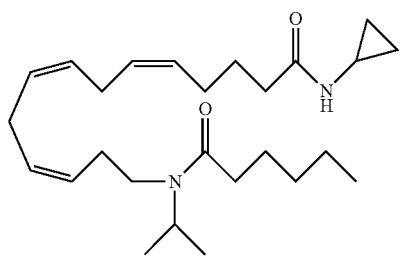

CMX020

Methods of producing CMX020 include at least one of Reactions I or II, preferably both.

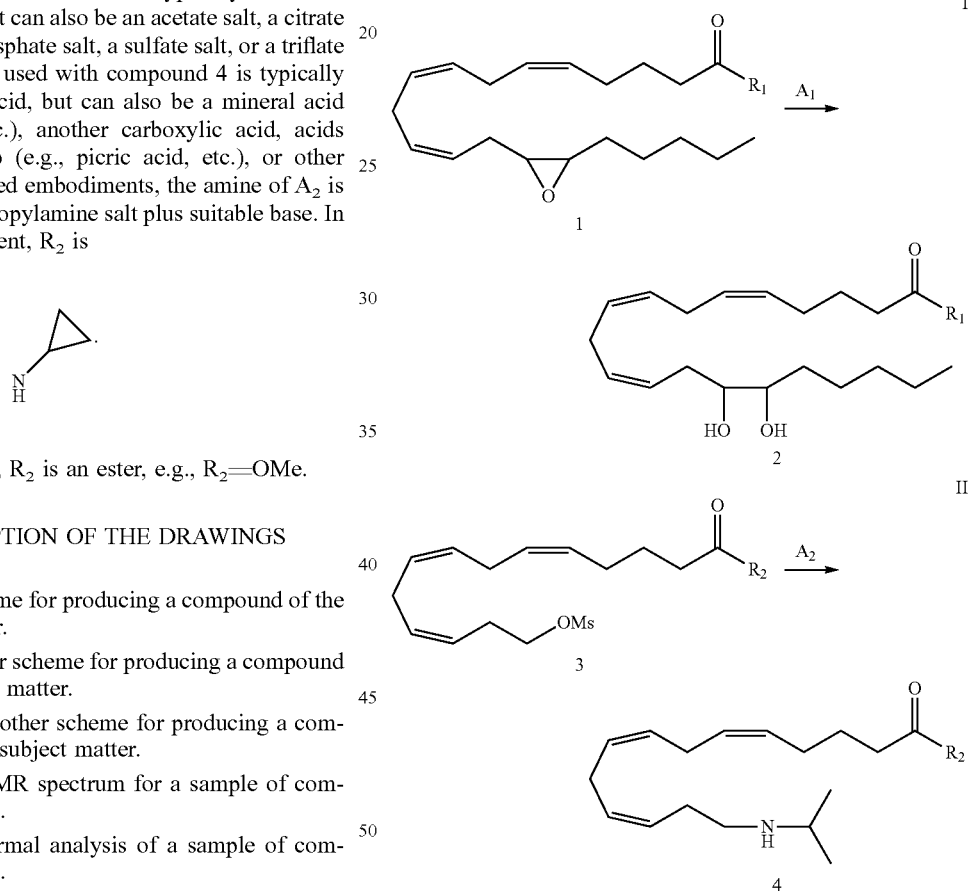

$R_1$ is typically a hydroxyl group, and $A_1$ generally applies one or more acids to compound 1. Where Reaction I is used, it is followed by the step of using either a metal base, preferably a lithium base, or an amine base with compound 2 to form an intermediate salt in crystalline form. Such an intermediate salt is further processed to produce CMX020, either directly or indirectly.

$R_2$ is typically a $C_3$-$C_6$ cycloalkyl substituted amine or a $C_5$-$C_6$ cycloalkenyl substituted amine (excluding enamines), and $A_2$ generally utilizes isopropylamine or an isopropylamine salt plus suitable base. Where Reaction II is used, it is followed by the step of using one or more acids with compound 4 to form an intermediate salt in crystalline form.

The acid of $A_1$ is preferably triflic acid, but other suitable acids are contemplated. When the amine of Reaction 1 is used, it is preferably (1R,2R)-(−)-1-amino-2-indanol, its enantiomer, or scalemic or racemic mixture thereof.

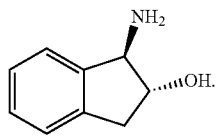 [SMILES: N[C@@H]1c2ccccc2C[C@H]1O]

Where more than one amine is used to complex with more than one compound 2, the amine can be present in racemic or scalemic ratios. When the metallic base of Reaction 1 is used, it is preferably one of a Group I or Group II metallic base, not including francium, radium, or hydrogen. Magnesium, cesium, nickel, or zinc could also be used as the metallic base.

The amine of $A_2$ is typically isopropylamine or an isopropylamine salt plus a suitable base. While $R_2$ can be an ester, e.g. OMe, in preferred embodiments $R_2$ is

though other cyclic or non-cyclic amines either substituted or not are contemplated. When Reaction II is used, whether or not in combination with Reaction I, the intermediate salt is typically an oxalate salt or a tosylate salt, though other salts such as an acetate salt, a citrate salt, a nitrate salt, a phosphate salt, a sulfate salt, or a triflate salt are contemplated. Viewed from another perspective, the acid of Reaction II is typically oxalic acid or tosylic acid, but can also be acetic acid, citric acid, nitric acid, phosphoric acid, sulfuric acid, or triflic acid.

Compositions including a salt of compound 2 are also contemplated.

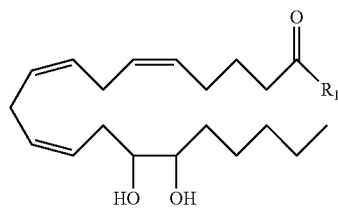

$R_1$ is typically a hydroxyl group and the salt is preferably one of a metal salt or an amine salt. The salt is crystalline in preferred embodiments.

Compositions comprising a salt of compound 4 are further contemplated.

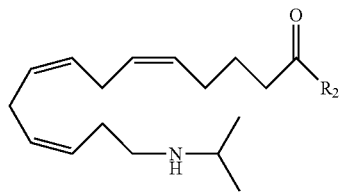

$R_2$ is typically a $C_3$-$C_6$ cycloalkyl substituted amine or a $C_5$-$C_6$ cycloalkenyl substituted amine (excluding enamines), preferably a N-cyclopropylamine, and the salt is an acid salt, preferably oxalate or tosylate. In preferred embodiments, the salt is crystalline.

Compositions and systems for delivering CMX020 or other AA analogs are further contemplated. A liposomal formulation of CMX020 includes an egg-phospholipid, a cholesterol oleate additive, and an ethanol solution of CMX020. Alternatives are contemplated, for example use of cholesterol linoleate, cholesterol polyunsaturated ester, or other suitable phospholipids, either alone or in combination with other phospholipids. Further, ethanol could be replaced or combined with DMSO, PEG (e.g., 100 dt to 10 dt), glycerol, or other pharmacologically suitable organic solvent. The egg-phospholipid is preferably L-α-Phosphatidylcholine, and a preferred ethanol solution of CMX020 has a ratio of 85.5:4.5:10 of phospholipid, cholesterol oleate additive, and CMX020, though alternative ratios of (phospholipid):(cholesterol oleate additive):(CMX020) are contemplated, including ratios or (90-80, 85-75, 70-60, 65-55, or 60-50):(1-3, 1.5-3.5, 2-4, 2.5-4.5, 3-5, 3.5-5.5, 4-6, or 4.5-6.5):(6-8, 8-10, 10-12, 12-14, or 15-20), as proportional combinations. When administered to rats via tail vein infusion, this formulation was found to have a half-life of 1.28 hrs.

Example 1

Further methods for producing 14,15-EET analogs and, in particular cases, CMX020 are also contemplated. For example, an IV drug product solution containing CMX020 (3 mg/mL, ≥97% purity), ascorbic acid (0.0135 mg/mL), and 2-hydroxypropyl-β-cyclodextrin (HPBCD) (200 mg/mL) in a diluent composed of 35% phosphate buffered saline (PBS)/65% sterile water for injection is contemplated.

Example 2

Oral drug products are also contemplated, for example having CMX020 (5% w/w) in docosahexaenoate triglyceride, alone or enriched, stabilized with α-tocopherols (3000 ppm). For some applications, oral drug products are filled into enterically coated softgel capsules.

Example 3

FIG. 1 depicts a scheme 100 for producing CMX020, compound 109, and can be adapted to produce further 14,15-EET analogs, with reference independent of.

Preparation of 103 (step b): To a stirring solution of arachidonic acid (102; 20.00 g, 65.7 mmol, 1.0 mol equiv) in $CH_2Cl_2$ (200 mL) at ambient under nitrogen was added 1,1'-carbonyldiimidazole (CDI; 11.72 g, 72.3 mmol, 1.1 mol equiv). After stirring overnight, a portion of the acylimidazole solution (184 mL, 20.53 g, 57.9 mmol) was added slowly via syringe pump (120 mL at 7 mL/h, followed by 64 mL at 9 mL/h) subsurface to a suspension of urea-hydrogen peroxide (UHP: 76.75 g, 14.1 mol equiv) and lithium imidazole (0.25 g, 3.4 mmol, 0.06 mol equiv) in $CH_2Cl_2$ (4.14 L, 13.4 mM final concentration) at ambient under nitrogen. After complete addition, the mixture was stirred overnight at ambient at which time HPLC indicated complete retention. Water (430 mL) was added and the biphasic mixture was stirred for 15 min. The organic phase was separated, washed sequentially with 1 M $KH_2PO_4$ (250 mL), 1 M $Na_2S_2O_3$ (250 mL) (no peroxide remaining), and water (250 mL). The solution was dried over $Na_2SO_4$, filtered, concentrated under reduced pressure, and remaining volatiles removed under high vacuum to afford crude 103 as a yellow oil (17.91 g) in 80.2% assay yield.

Alternatively, epoxidation of the 14, 15 olefin of 102 by (i) application of an engineered cytochrome P450 BM3 ("BM3") for efficient enzymatic epoxidation, (ii) using peroxide for the epoxidation step, or (iii) combining the epoxidation step with in situ hydrolysis of the epoxide by soluble epoxide hydrolase ("sEH"). Preferably, the sEH step is simultaneous with the BM3 epoxidation, or in a stepwise, one-pot cascade. For example, the sEH is added to the reaction media after the epoxidation is complete, but before product isolation. This favorably provides direct access to the lithium salt-diol.

Chromatography: 900 mgs of crude 103 loaded onto a pre-packed 220 g CombiFlash column and eluted for 5 min using 5% EtOAc/hexanes, 6-10 min using 10% EtOAc/hexanes, and finally a gradient of 10% to 25% EtOAc/hexanes over 15 min. Fraction volume=18 mL. Product eluted in fraction #35. No useful resolution of 11,12-EET impurity.

Methyl ester of 103: $^1$H NMR ($CDCl_3$, 400 MHz) δ 5.59-5.34 (m, 6H), 3.67 (s, 3H), 2.99-2.86 (m, 2H), 2.85-2.75 (m, 4H), 2.45-2.01 (m, 6H), 1.70-1.65 (pentet, J=7.4 Hz, 2H), 1.57-1.24 (m, 8H), 0.90 (t, J=7.1 Hz, 3H).

Preparation of 104 (step c): To a stirring, 2° C. solution of crude 103 (13.90 g) in THF (24 mL) under nitrogen was added a 1 M aq. solution of trifluoromethanesulfonic acid (8 mmol, 8 mL, 1.1 mol equiv) dropwise over 10 min while maintaining <5° C. reaction temperature. The cooling bath was removed and the solution stirred at ambient. After 4 h, the reaction mixture was cooled (3° C.), quenched with sat. $NaHCO_3$ (38 mL) and extracted with methyl tert-butyl ether (MTBE; 76 mL). The organic layer was washed with water (38 mL), dried over dried over $Na_2SO_4$, filtered, concentrated under reduced pressure, and remaining volatiles removed under high vacuum to afford crude diol acid 104 as an oil (13.18 g, 81.6% assay yield).

Lithium Salt: Diol acid (2.00 g, 5.9 mmol) was completely dissolved in MeOH (10 mL, 1-2 hrs) at ambient. LiOH (145 mg, 5.9 mmol) was added and the solution stirred for 1 h at ambient. $CH_3CN$ (20 mL) was added slowly to the stirring solution, then seeded with crystalline Li salt (~10 mg). The seed held and more $CH_3CN$ (20 mL) was added. After stirring overnight at ambient, filtration and drying under nitrogen afforded the Li salt (1.62 g, 94.5 LCA %, 79% isolated) contaminated with 2.2% of the 11,12-regioisomer (no rejection of impurity during crystallization), mp 155.2° C., fine white, non-hydroscopic solid. NB: 2-Propanol gave a 78% recovery with a marked reduction in the 11,12-impurity and is thus the preferred solvent for recrystallization.

Regeneration of free acid of 104: To a solution of lithium salt (0.80 g, 1 equiv) in $H_2O$ (50 mL) was added aq. HCl (0.3 M, 7.75 mL, 2.3 mmol, 1 equiv). The solution was then extracted using EtOAc/heptane (1:1, 4×50 mL). The combined organic extracts were washed with brine (50 mL), dried over $MgSO_4$, filtered and concentrated under reduced pressure to give the free acid of 104 (0.50 g, 63.6% yield).

Methyl ester of 104: $^1$H NMR ($CDCl_3$, 400 MHz) δ 5.60-5.29 (m, 6H), 3.66 (s, 3H), 3.52-3.42 (m, 2H), 2.88-2.76 (m, 4H), 2.31 (t, J=7.5 Hz, 4H), 2.16-2.08 (m, 4H), 1.70-1.65 (pentet, J=7.3 Hz, 2H), 1.59-1.20 (m, 8H), 0.89 (t, J=7.1 Hz, 3H).

Preparation of 105 (step d): To a stirring, ambient DMF (4 mL) solution of recrystallized diol acid 104 (0.64 g, 1.9 mmol, 1.0 equiv), di-isopropylethylamine (DIPEA; 0.33 mL, 1.9 mmol, 1.0 equiv), and cyclopropylamine (0.19 mL, 2.5 mmol, 1.3 equiv) in DMF (4 mL) was added EDCI (0.44 g, 2.8 mmol, 1.5 equiv) as a solid in 5 portions over 5 min under nitrogen. After 16 h, the reaction was diluted with EtOAc (50 mL), heptane (50 mL), and water (50 mL). After the split, the aqueous phase was re-extracted with EtOAc/heptane (1:1, 100 mL). The combined organic phases were washed with water (50 mL), dried over $MgSO_4$, filtered, concentrated under reduced pressure, and remaining volatiles removed under high vacuum to afford 105 as a yellowish oil (0.56 g, 1.5 mmol, 78.5% yield).

Preparation of 106 (step e): To a stirring, 0° C. solution of 105 (0.35 g, 0.9 mmol, 1.0 equiv) in MeOH (7 mL) was added dropwise an aq. solution of $NaIO_4$ (2.10 mL, 0.113 g/mL, 1.1 mmol, 1.2 equiv) under nitrogen. After 1 h, the reaction mixture was filtered through a short pad of Celite and the pad was washed with additional MeOH (5 mL). An aq. solution of $NaBH_4$ (1.0 mL, 0.035 g/mL, 0.9 mmol, 1.0 equiv) was added with to the filtrate at 0° C. under nitrogen. The reaction was quenched by addition of 0.3 N aq. HCl (25 mL, 7.5 mmol, 8.3 mol equiv). The reaction mixture was concentrated to 20 mL under reduced pressure and extracted with MTBE (100 mL). After the split, the aqueous phase was re-extracted with MTBE (100 mL). The combined organic phases were washed with brine (50 mL), dried over $MgSO_4$, filtered, concentrated under reduced pressure, and remaining volatiles removed under high vacuum to afford alcohol 106 as a yellowish oil (0.25 g, 0.9 mmol, 97.2% yield, uncorrected for wt % purity).

Preparation of 107 (step f): To a stirring, ambient solution of 106 (251 mg, 0.91 mmol, 1.0 equiv) in $CH_2Cl_2$ (1 mL) was added trimethylamine (TEA; 0.316 mL, 2.265 mmol, 2.5 equiv) followed by MsCl (0.105 mL, 1.359 mmol, 1.5 equiv). After 6 h, the mixture was quenched with saturated aq. $NaHCO_3$ (5 mL), diluted with water (25 mL), and extracted with $CH_2Cl_2$ (50 mL). The aqueous phase was re-extracted with $CH_2Cl_2$ (25 mL). The combined organic phases were washed with brine (25 mL), dried over $MgSO_4$, filtered, concentrated under reduced pressure, and remaining volatiles removed under high vacuum to afford mesylate 107 as a brown oil (300 mgs, 89% yield, uncorrected for wt % purity).

Preparation of 108 (step g): To a stirring 0° C. solution of mesylate 107 (251 mgs, *HPLC AUC 84%, 1.0 equiv) was added $Et_3N$ (0.50 mL, 12 equiv) and isopropylamine (0.30 mL, 6 equiv). The mixture was sealed and heated to 40° C. for 48 h at which point HPLC analysis indicated 5% of 107 remained. Alternatively, the reaction in 10×DMF went to completion in 8 h at 60° C. (no additional details available). The reaction was quenched with water (25 mL) and extracted with EtOAc (25 mL). The water phase was re-extracted with EtOAc (25 mL). The combined extracts were washed with brine (25 mL), dried over $MgSO_4$, filtered, concentrated under reduced pressure, and remaining volatiles removed under high vacuum to afford isopropylamine 108 (153 mgs) as a brown oil (HPLC AUC 85%). In some embodiments, it is preferred to crystalize crude 108 as oxalate or tosylate salts.

Preparation of CMX020, 109 (step h): To a stirring, ambient MTBE (1 mL) solution of crude 108 (153 mgs, 0.408 mmol, 1 equiv) under nitrogen was added $Et_3N$ (0.316 mL, 2.27 mmol, 5.56 equiv) followed by dropwise addition of hexanoyl chloride (0.19 mL, 1.36 mmol, 3.33 equiv). After 2 h, the reaction was quenched with sat. aq. $NaHCO_3$ (5 mL), diluted with water (25 mL), and extracted with MTBE (25 mL). The water phase was re-extracted with MTBE (25 mL). The combined extracts were washed with brine (25 mL), dried over $MgSO_4$, filtered, concentrated under reduced pressure, and remaining volatiles removed under high vacuum to afford CMX020, 109, (350 mgs) as a brown oil. Chromatographic purification using 50% EtOAc/hexanes then 60% EtOAc/hexanes afforded CMX020 (113 mgs, HPLC AUC 96%) in 64% yield from diol 104. TLC: 50% EtOAc/hexanes, $R_f$~0.45; $CHCl_3$/hexanes/acetone (10:10:3), $R_f$~0.41.

$^1$H NMR: Complex spectrum due to two major rotational isomers (rotamers) about the two amides. $^1$H NMR spectrum features two bisallylic methylenes, two sets of cyclopropyl methylenes, two sets of isopropyl methines, and two NH signals. $^{13}$C NMR spectrum includes 4 carbonyl carbons and 12 vinyl carbons. See spectrum file. $^1$H NMR ($CDCl_3$, 300 MHz, ~3:2 mixture of rotamers) δ 6.40 (br s, 1H), 5.98 (br s, 1H), 5.29-5.44 (m, 6H), 4.61-4.67 and 4.00-4.08 (m, 1H for two rotamers), 3.09-3.16 (m, 2H), 2.88 and 2.92 (s, 1H for two rotamers), 2.75-2.85 (m, 4H), 2.64-2.74 (m, 1H), 2.25-2.36 (m, 4H), 2.03-2.15 (m, 4H), 1.58-1.73 (m, 4H), 1.30-1.34 (m, 4H), 1.18 and 1.13 (d, J=6.7 Hz, 6H for two rotamers), 0.87 (t, J=6.6 Hz, 3H), 0.70-0.75 (m, 2H).

Non-Chromatographic Purification: By utilizing a recrystallized (pure) 108 (and compound 104 above), pure CMX020 is successfully produced by appropriate acid-base extraction procedure (aka pH extraction).

Example 4

Figure 2:
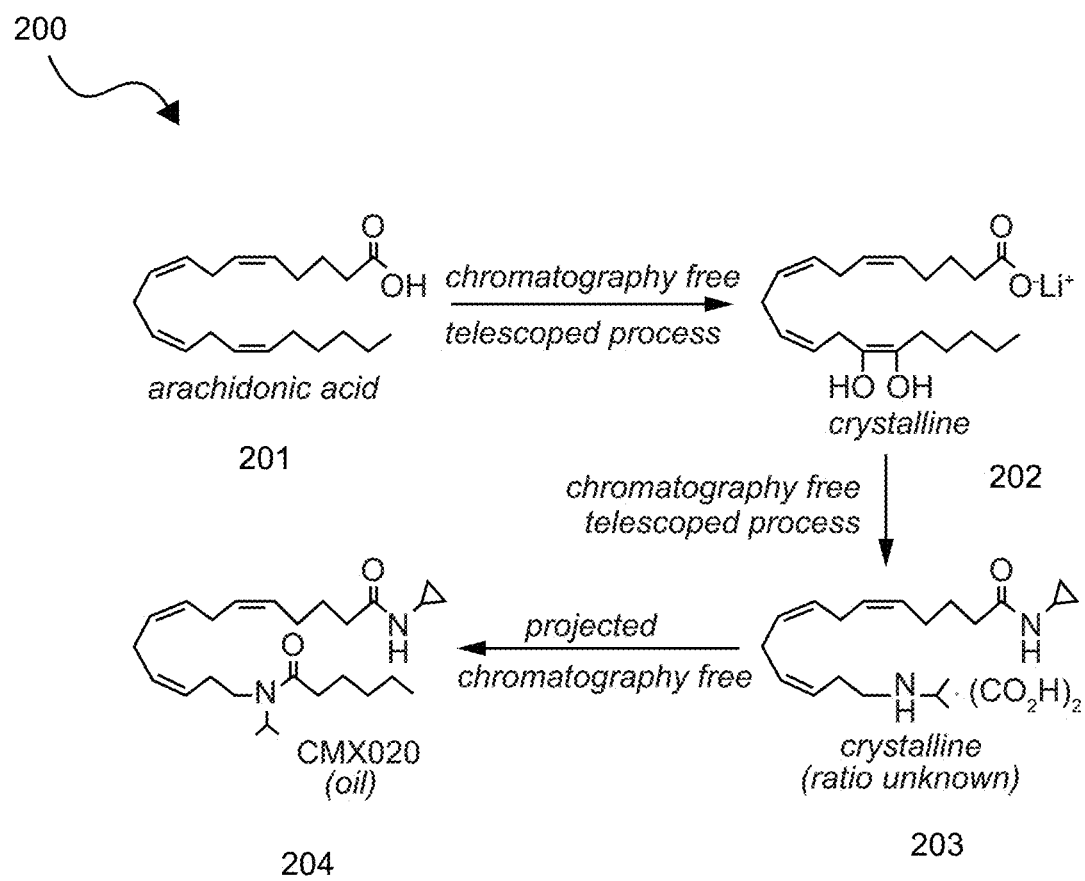
FIG. 2 depicts another scheme for producing a compound of the inventive subject matter.

FIG. 2 depicts a telescoped process route 200 of using compounds 201, 202, and 203 to produce CMX020, compound 204, without requiring chromatographic processing. It should be appreciated that postponing chromatographic purification after each individual reaction procedure (step) and conducting the purification either by chromatography or crystallization after 2 or more steps increases overall efficiency and yield, and reduces the cost and processing time.

Example 5

Figure 3:
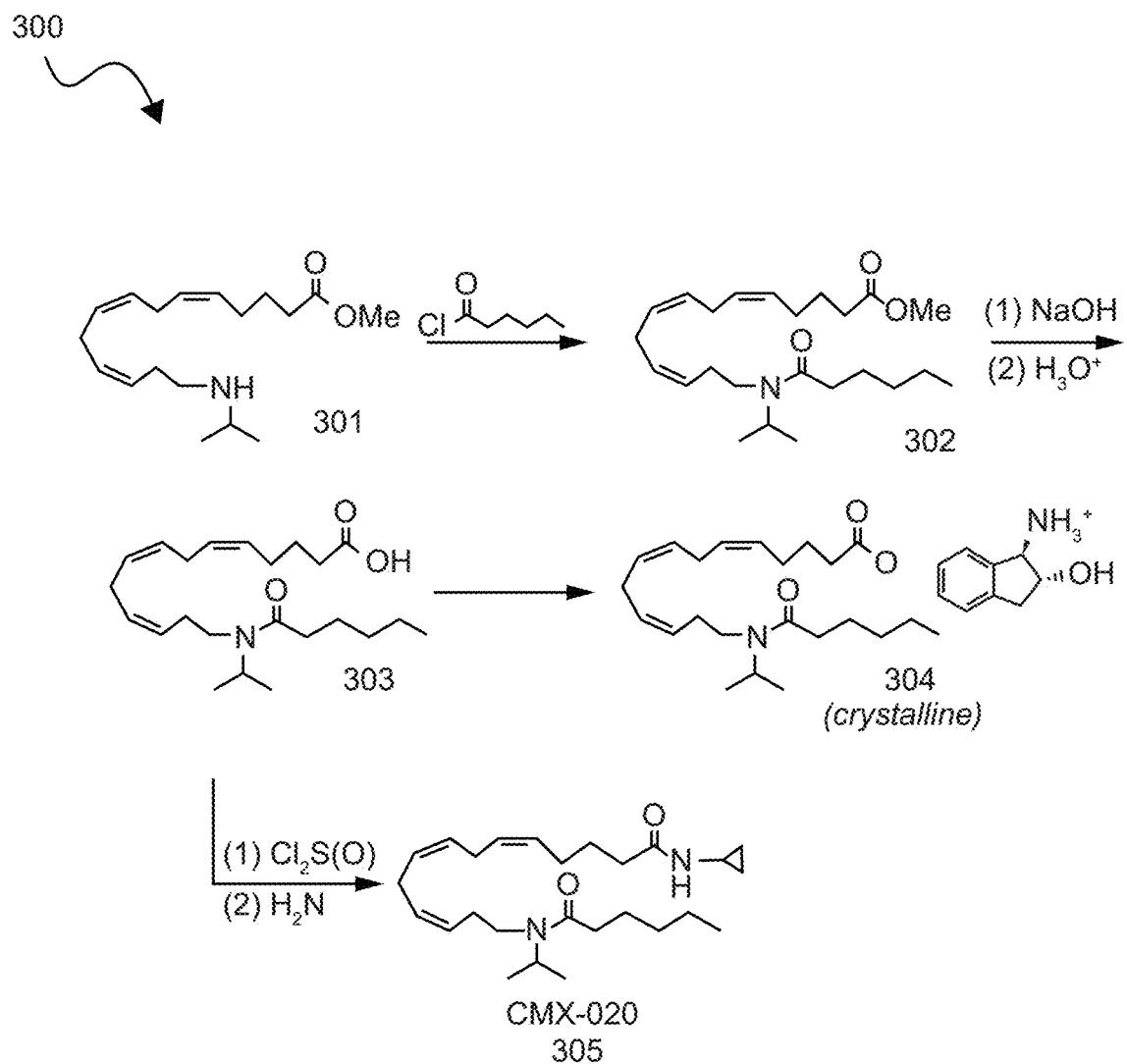
FIG. 3 depicts yet another scheme for producing a compound of the inventive subject matter.

FIG. 3 depicts scheme 300 for producing CMX-020, compound 305, and can be adapted to produce further AA analogs.

To a stirring solution of crude methyl ester 301 (3.53 g crude mass, 12 mmol, 1.0 mol equiv) in MTBE (40 mL) under nitrogen was added $Et_3N$ (2.17 mL, 15.6 mmol, 1.3 mol equiv). The solution was cooled (2° C.) and hexanoyl chloride (2.01 mL, 14.4 mmol, 1.2 mol equiv) was added dropwise over 15 min, maintaining temperature <5° C. The reaction was stirred at temperature <10° C. After 2.5 h, HPLC analysis showed that a small amount of methyl ester 301 (1.7% area %, HPLC) remained, so additional $Et_3N$ (0.17 mL, 1.2 mmol, 0.1 mol equiv) and hexanoyl chloride (0.17 mL, 1.2 mmol, 0.1 mol equiv) were added and the reaction was stirred for 30 min. The reaction was removed from the cooling bath, 1 N HCl (5 mL) was added, and stirred for 1 h. The layers were separated and the organic layer was washed with aq. 1 N HCl (2×5 mL), aq. 0.1 N NaOH (5 mL), and brine (5 mL). The organic layer was dried over $Na_2SO_4$, filtered, concentrated under reduced pressure, and dried under high vacuum to afford amide 302 (4.74 g, 12.1 mmol, 96.0 area %, HPLC) as an oil in 100.9% yield, uncorrected for wt % impurity.

To a stirring, cooled (2° C.) solution of crude amide 302 (4.63 g crude mass, 11.8 mmol, 1.0 mol equiv, assumed 100% from intermediate 106 in FIG. 1 and charges of reagents based upon this number) in MeOH (20 mL) under nitrogen was added a solution of NaOH (1.89 g, 47.2 mmol, 4.0 mol equiv in 5.5 mL H2O) dropwise, maintaining temperature <5° C. The reaction mixture was stirred for 30 min, then warmed to ambient temperature for 1.5 h, at which time HPLC showed the reaction was complete (<1 area % 302 remaining). Water (60 mL) was added while stirring, and an increase in temperature from ~18° C. to 25° C. was observed. The aqueous phase was washed with MTBE (10 mL) and heptane (20 mL). The aqueous layer was acidified with aq. 3 N HCl (20 mL; pH of aqueous layer=1-2) and extracted with MTBE (3×20 mL). The organic layers were combined and washed with water (20 mL), dried over Na2SO4, filtered, concentrated under reduced pressure, and dried under high vacuum to afford carboxylic acid C (4.32 g, 11.4 mmol, 97.1 LCA %, HPLC) as an oil in 96.8% yield uncorrected for wt % impurity. Crude 303 was assayed by $^1$H NMR employing an internal standard (mesitylene, 98%) and was determined to be 93.7 wt %.

Mixing 303 (130.1 mg, 0.3 mmol) and (1R,2R)-(−)-trans-1-amino-2-indanol (53.0 mg, 0.3 mmol) in $CH_3CN$ resulted in a solid precipitate that appears to be a 1:1 salt. HPLC shows the salt is 95.1 area % and this fits with $^{13}$C NMR.

To a stirring solution of crude 303 (500.5 mg crude, 1.3 mmol) in isopropyl acetate (IPAc: 5 mL) at ambient temperature under nitrogen was added 1,1'-carbonyldiimidazole (CDI: 236.4 mg, 1.5 mmol, 1.1 mol equiv). After 1.5 h, additional CDI (107.8 mg, 0.7 mmol, 0.5 mol equiv) was added. After 1 h, cyclopropylamine (0.28 mL, 4.0 mmol; 3.0 mol equiv) was added and the reaction was complete in 30 min as indicated by HPLC. The reaction was filtered and the solids were washed with IPAc (5 mL). Additional IPAc (25 mL) was added and the organic layer was washed with aq. 1 N HCl (30 mL) and water (30 mL), dried over $Na_2SO_4$, filtered, and concentrated under reduced pressure, and dried under high vacuum to afford CMX-020, 305, (512.0 mg, 1.2 mmol, 95.3 area %, HPLC) as an oil in 92.4% yield uncorrected for wt % purity. $^1$H NMR assay using an internal standard (mesitylene, 98%) indicated 85.0 wt %.

Figure 4:
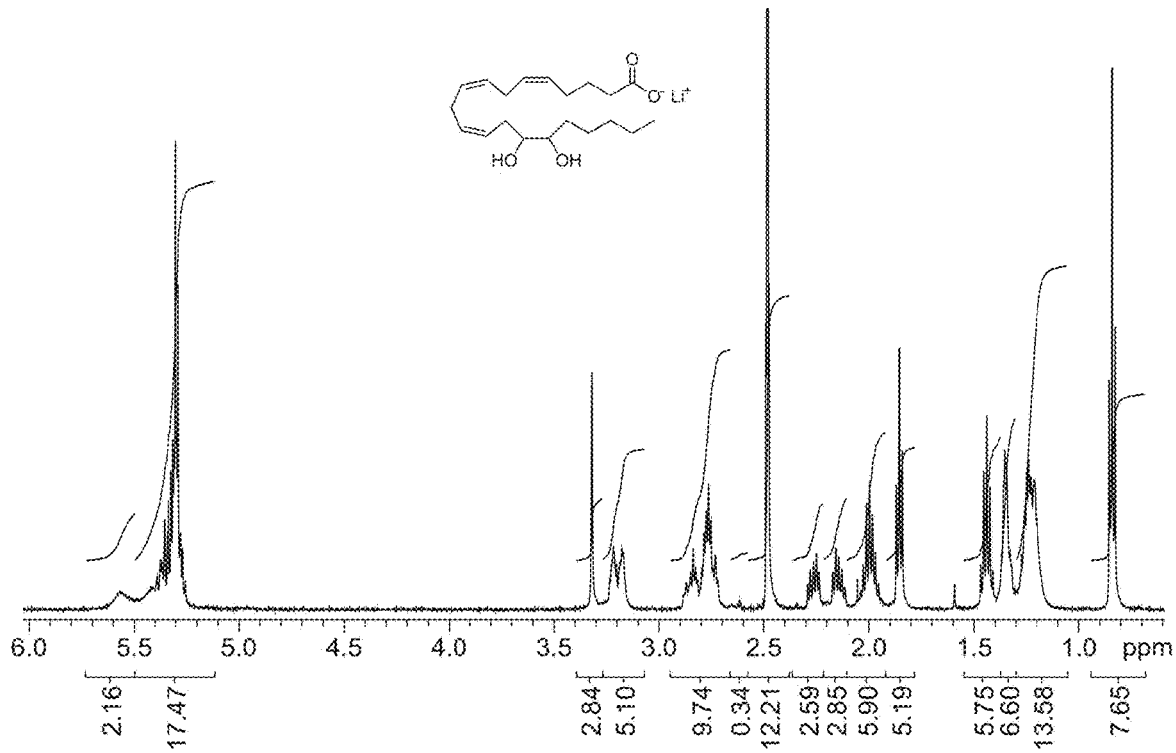
FIG. 4 depicts an NMR spectrum for a sample of compound 202 from FIG. 2.

FIG. 4 is the NMR spectrum for a sample of compound 202 from FIG. 2.

Figure 5:
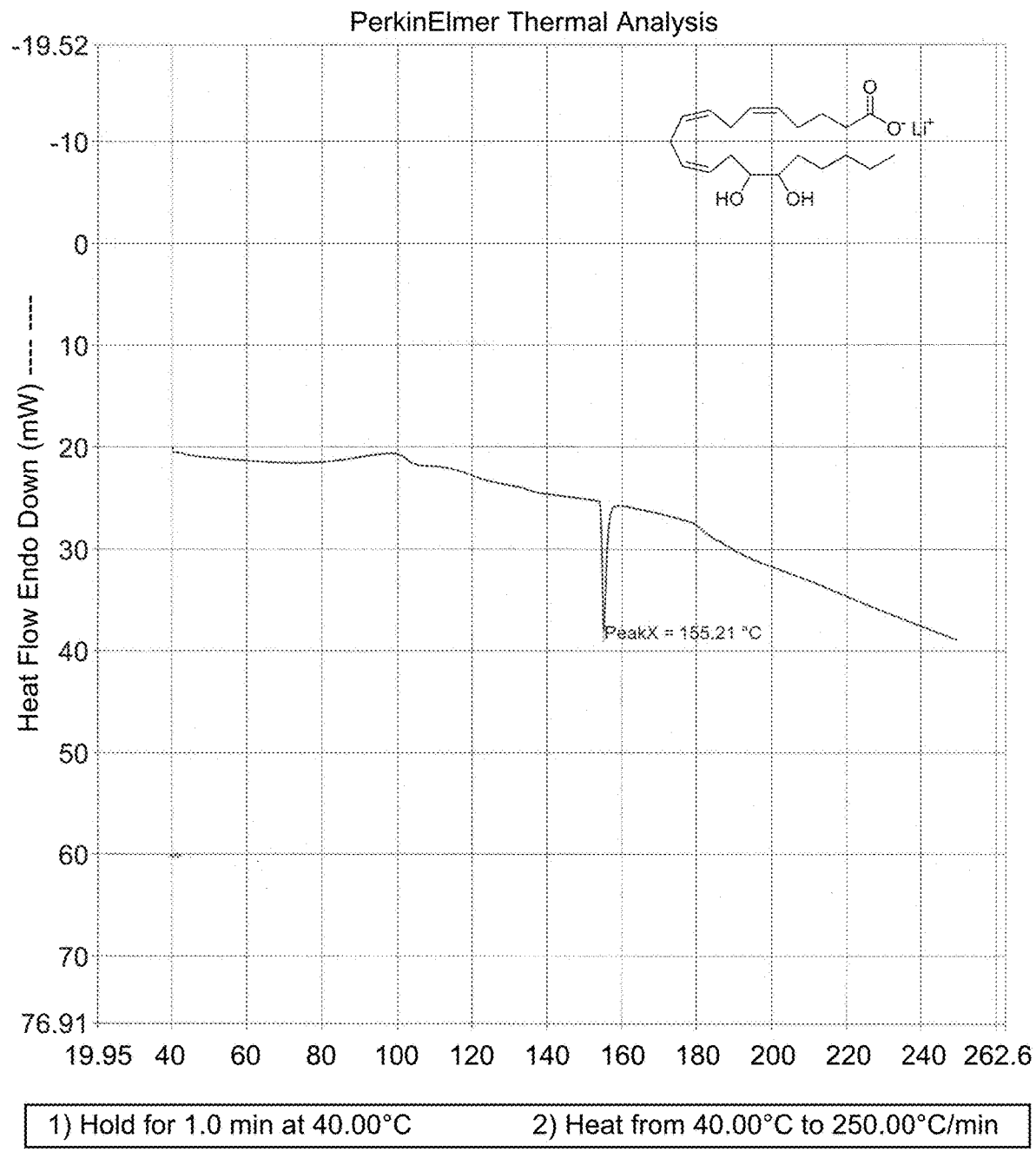
FIG. 5 depicts a thermal analysis of a sample of compound 202 from FIG. 2.

FIG. 5 is a thermal analysis of a sample of compound 202 from FIG. 2.

Figure 6:
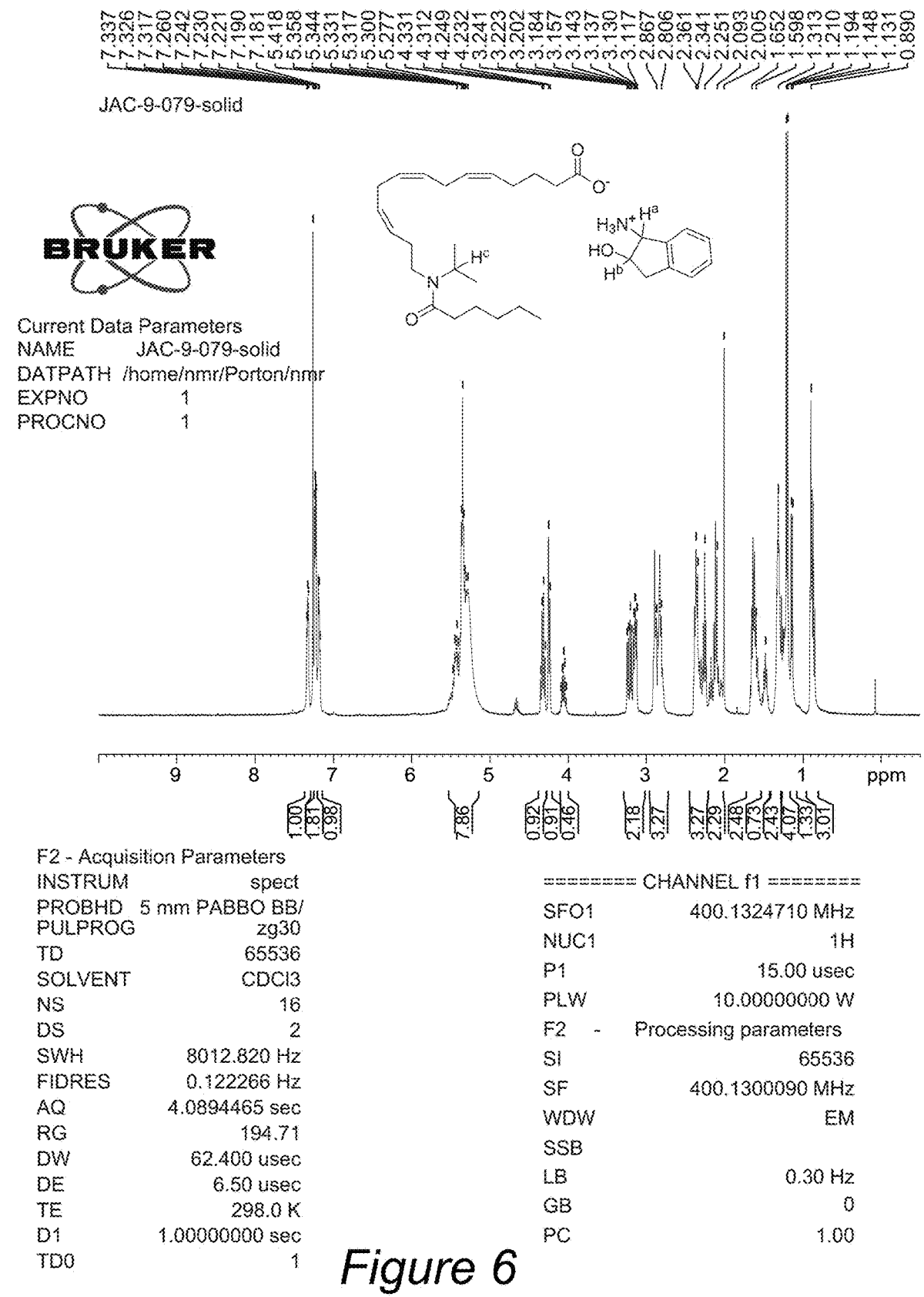
FIG. 6 depicts an NMR spectrum for a sample of compound 304 from FIG. 3.

FIG. 6 is the NMR spectrum for a sample of compound 304 from FIG. 3.

Figure 7:
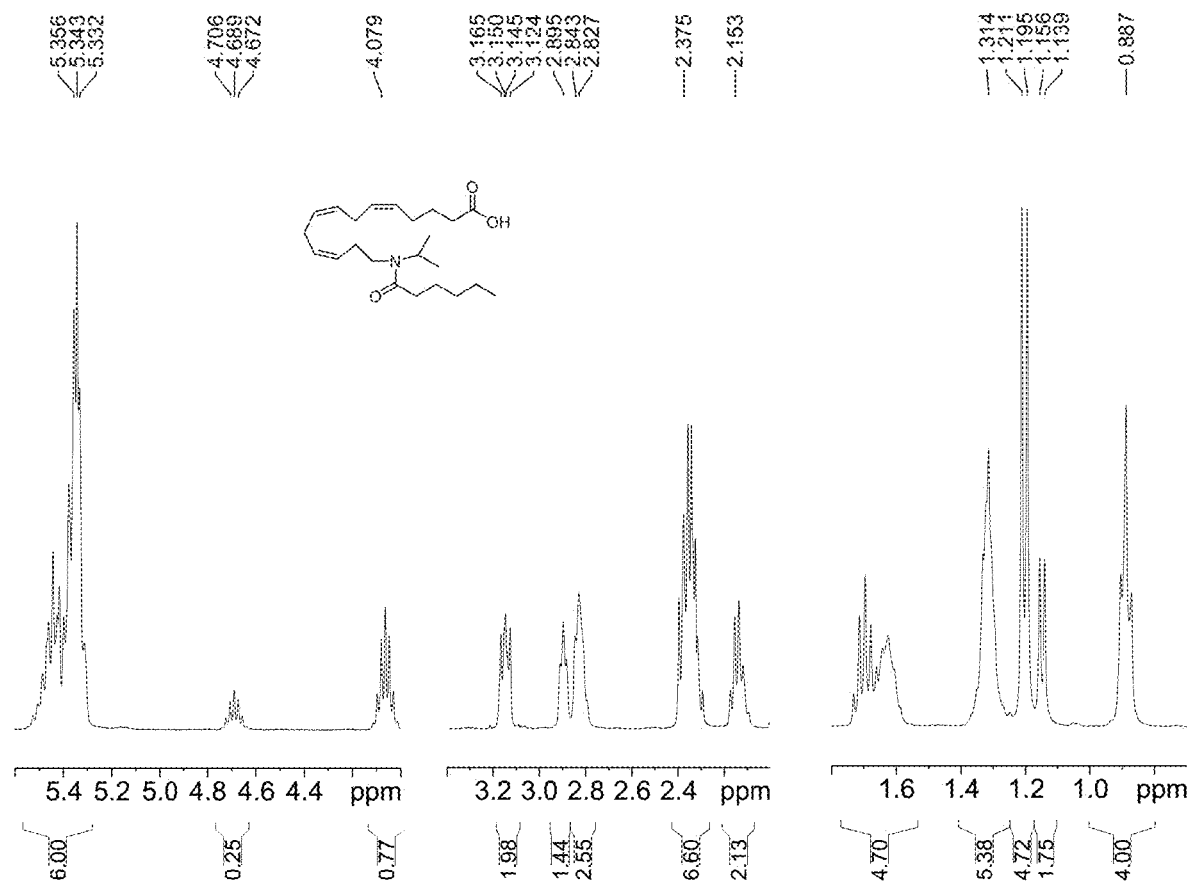
FIG. 7 depicts an NMR spectrum for a sample of a free acid of compound 304 from FIG. 3.

FIG. 7 is the NMR spectrum for a sample of a free acid of compound 304 from FIG. 3.

The following description includes information that may be useful in understanding the present invention. It is not an admission that any of the information provided herein is prior art, necessary, or relevant to the presently claimed invention, or that any publication specifically or implicitly referenced is prior art.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:
1. A method of providing a first intermediate salt, comprising the steps of:

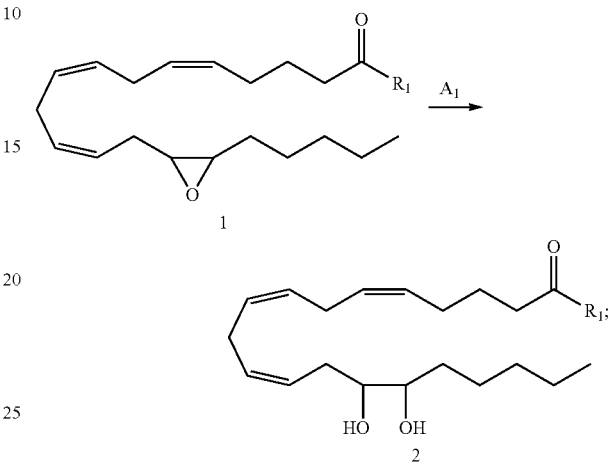

and
using one of a metallic base or a first amine base with compound 2 to form the first intermediate salt; and
purifying the first intermediate salt by crystallization,
wherein $A_1$ applies a first acid, and $R_1$ is a hydroxyl group, and the first intermediate salt is crystalline.

2. The method of claim 1, wherein the acid of $A_1$ is triflic acid.

3. The method of claim 1, wherein a first amine base is used with compound 2 to form the first intermediate salt.

4. The method of claim 3, wherein the first amine base is:

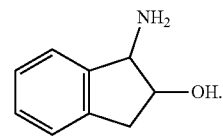 [SMILES: NC1c2ccccc2CC1O]

5. The method of claim 1, wherein the metallic base is used with compound 2 to form the first intermediate salt.

6. The method of claim 1, wherein the metallic base is selected from the group consisting of a Group I or Group II metallic base, and wherein the metallic base is not selected from the group consisting of hydrogen, francium, and radium.

7. The method of claim 1, further providing a second intermediate salt, further comprising the steps of:

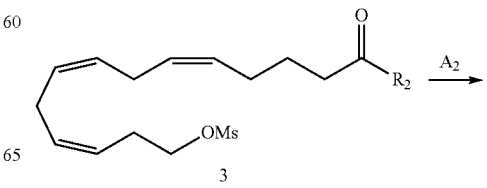

-continued

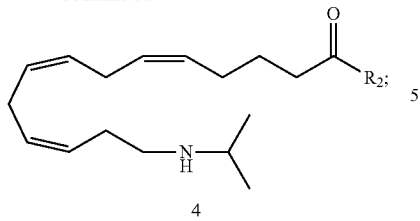

and using a second acid with compound 4 to form the second intermediate salt; and purifying the second intermediate salt by crystallization, wherein $A_2$ applies a second amine base selected from the group consisting of (i) isopropylamine and (ii) isopropylamine salt with a suitable base, and $R_2$ is selected from the group consisting of a $C_3$-$C_6$ cycloalkyl substituted amine, a $C_5$-$C_6$ cycloalkenyl substituted amine (excluding enamines), and an ester, and wherein the second intermediate salt is crystalline;

and wherein compound 3 is derived from compound 2.

8. The method of claim 7, wherein the second intermediate salt is selected from the group consisting of an oxalate salt, a tosylate salt, a mineral salt, a carboxylic salt, and a salt having a phenyl group.

9. The method of claim 7, wherein the second acid is selected from the group consisting of oxalic acid, tosylic acid, a mineral acid, a carboxylic acid, and an acid having a phenyl group.

10. The method of claim 7, wherein the second amine base is isopropylamine.

11. The method of claim 7, wherein $R_2$ is

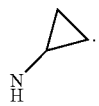

12. The method of claim 7, wherein the second intermediate salt produced by reaction of compound 4 with the second acid is compound CMX020,

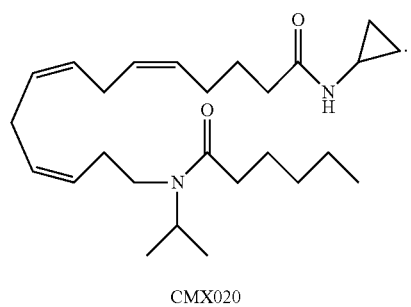 [SMILES: CCCCCC(=O)N(CC/C=C\C/C=C\C/C=C\CCCC(=O)NC1CC1)C(C)C]

CMX020

13. The method of claim 12, wherein the acid is triflic acid.

14. The method of claim 7, wherein the second amine base is:

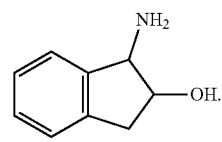 [SMILES: NC1c2ccccc2CC1O]

15. The method of claim 12, wherein the first metallic base is used with compound 2 to form the first intermediate salt.

16. The method of claim 12, wherein the metallic base is selected from the group consisting of a Group I and a Group II metallic base, and wherein the metallic base is not selected from the group consisting of hydrogen, francium, and radium.

17. The method of claim 12, wherein the second intermediate salt is one of an oxalate salt, a tosylate salt, a mineral salt, a carboxylic salt, or a salt having a phenyl group.

18. The method of claim 12, wherein the second acid is selected from the group consisting of oxalic acid, tosylic acid, a mineral acid, a carboxylic acid, and an acid having a phenyl group.

19. The method of claim 12, wherein the step of $A_2$ applies isopropylamine.

20. The method of claim 12, wherein $R_2$ is

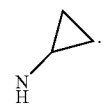

21. A composition comprising a salt of compound 2:

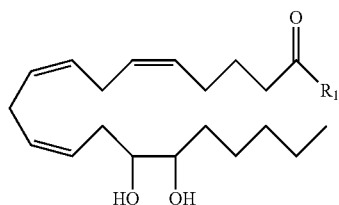

wherein $R_1$ is a hydroxyl group and the salt is selected from the group consisting of a metal salt and an amine salt, and wherein the salt is crystalline.

22. A composition comprising a salt of compound 4:

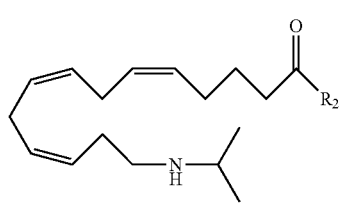

wherein $R_2$ is selected from the group consisting of a $C_3$-$C_6$ cycloalkyl substituted amine, a $C_5$-$C_6$ cycloalkenyl substituted amine (excluding enamines), and ester, and wherein the salt is an acid salt, wherein the salt is crystalline.

23. The method of claim 1, wherein the metallic base is selected from the group consisting of a Group I or Group II metallic base.

24. The method of claim 12, wherein the metallic base is selected from the group consisting of a Group I or Group II metallic base.

* * * * *